(12) United States Patent
Huang et al.

(10) Patent No.: US 10,064,539 B2
(45) Date of Patent: Sep. 4, 2018

(54) INSPECTION POSITIONING PROSTATIC CAPSULE EXPANSION CATHETER

(71) Applicants: NANJING SHUANGWEI BIOTECHNOLOGY CO., LTD., Nanjing (CN); Zheng Huang, Nanjing (CN); Weiguo Huang, Nanjing (CN)

(72) Inventors: Zheng Huang, Nanjing (CN); Weiguo Huang, Nanjing (CN); Min Ma, Nanjing (CN)

(73) Assignee: Nanjing Shuangwei Biotechnology Co., Ltd., Nanjing (CN)

( * ) Notice: Subject to any disclaimer, the term of this patent is extended or adjusted under 35 U.S.C. 154(b) by 907 days.

(21) Appl. No.: 14/257,504

(22) Filed: Apr. 21, 2014

(65) Prior Publication Data

US 2015/0297061 A1 Oct. 22, 2015

(51) Int. Cl.
*A61B 1/00* (2006.01)
*A61M 25/10* (2013.01)
*A61B 1/05* (2006.01)

(52) U.S. Cl.
CPC ...... *A61B 1/00082* (2013.01); *A61B 1/00177* (2013.01); *A61B 1/05* (2013.01); *A61M 25/1002* (2013.01); *A61M 25/1011* (2013.01); *A61M 2210/166* (2013.01)

(58) Field of Classification Search
CPC .......... A61B 1/00082; A61M 25/1002; A61M 2210/166
See application file for complete search history.

(56) References Cited

U.S. PATENT DOCUMENTS 5,263,931 A * 11/1993 Miller ................ A61B 1/00082
604/103.1
2012/0302826 A1* 11/2012 Copa .................... A61M 5/3007
600/104

FOREIGN PATENT DOCUMENTS

CN 102000384 4/2011
CN 202982896 6/2013

* cited by examiner

*Primary Examiner* — Nathan R Price
*Assistant Examiner* — Melissa A Snyder
(74) *Attorney, Agent, or Firm* — Rankin, Hill & Clark LLP

(57) ABSTRACT

An inspection positioning prostatic capsule expansion catheter includes a catheter main body. The catheter main body is internally provided with a catheterization cavity, a rinse cavity, a front bag cavity, and a rear bag cavity. The four cavities are each provided with a front-end opening. At the rear of the front-end openings of the catheterization cavity and the rinse cavity is the front bag cavity. At the rear of the front bag cavity is the rear bag cavity arranged in parallel. The catheter main body at the tail of the rear bag cavity is provided with a miniature visual probe. The miniature visual probe is mounted on a semi-circular protrusion at the tail of the rear bag cavity.

10 Claims, 1 Drawing Sheet

INSPECTION POSITIONING PROSTATIC CAPSULE EXPANSION CATHETER

BACKGROUND

Technical Field

The present application relates to a prostatic capsule expansion catheter, and particularly to an inspection positioning prostatic capsule expansion catheter.

Related Art

At present, among many prostate surgeries, treatment of prostatic hyperplasia by using a prostatic capsule expansion technology is the only one that retains the original organ, retains the original function, has minimal trauma and is highly safe. The technology wins Chinese medical and health care "outstanding achievement" award, and is worthy of research and promotion.

Front-end openings 1B and 2B of a catheterization cavity and a rinse cavity of a prostatic splitting catheter in the prior art are provided with a composite columnar high-pressure water bag consisting of an inner bag 5 and an outer bag 6, as shown in FIG. 1. The prior art has the following disadvantages: 1. the inner bag is hidden in the outer bag, and positioning is blind; 2. the structure is complicated, and once the bag ruptures, the patient bleeds a lot, and the catheter must be replaced; 3. the postoperative catheter cannot be fastened and is easy to slip, and if it is fastened through water injection by a columnar outer bag, the patient is painful; 4. the catheterization cavity only has one front-end side hole, and thus drainage is not smooth and it is easily blocked by clots; 5. it is difficult to maintain pressure in the bags; 6. regular decompression after the operation is tedious; 7. the columnar water bag compresses and injures seminal colliculus; and 8. the surgical site cannot be seen during positioning, and operations merely rely on experience of a surgeon. As the prostatic splitting catheter has the above problems, the treatment effect and quality are seriously affected.

SUMMARY

To solve the above problems, the present application provides an inspection positioning prostatic capsule expansion catheter that achieves clear and accurate positioning, is not easy to slide after the positioning, has good expansion effects, can protect seminal colliculus from compression and injury by high-pressure water bags, and is easily operated during operation and after operation.

The objective of the present application is implemented through the following technical solution: an inspection positioning prostatic capsule expansion catheter, including a catheter main body, where the catheter main body is internally provided with a catheterization cavity, a rinse cavity, a front bag cavity, and a rear bag cavity; the four cavities are each provided with a front-end opening, at the rear of the front-end openings of the catheterization cavity and the rinse cavity is the front bag cavity, and at the rear of the front bag cavity is the rear bag cavity arranged in parallel; the catheter main body at the tail of the rear bag cavity is provided with a miniature visual probe, and the miniature visual probe is mounted on a semi-circular protrusion at the tail of the rear bag cavity.

The miniature visual probe is 1-2 cm from the tail of the rear bag cavity. The front-end opening of the catheterization cavity is two holes, and the two holes are 7 mm in length and 3-5 mm in width; and the front-end opening of the rinse cavity is a single hole, and the single hole is a 1.5×1.5 mm square hole or a round hole with a diameter of 1.5 mm.

The catheter main body has a length of 38 cm, and an outer diameter of 0.7 cm; the front bag cavity is barrel-shaped after filling, and has a length of 3 cm; the rear bag cavity is barrel-shaped or arched after filling and has a length of 4-10 cm; during filling, the front and rear bag cavities have outer diameters of 3.2-3.9 cm The barrel-shaped front bag cavity and the barrel-shaped or arched rear bag cavity both can withstand a pressure greater than or equal to 0.48 MPa. Water injection catheters of rear-end openings of the front bag cavity and the rear bag cavity are externally connected with two-way or three-way switches, and are then connected with pressure gauges.

A wash pipe connected to a rear-end opening at the tail of the catheter main body is 15 cm in length, a water injection catheter connected to a rear-end opening of the front bag cavity is 50 cm in length, and a water injection catheter connected to a rear-end opening B4 of the rear bag cavity is 40 cm in length.

In addition, the miniature visual probe is connected with a bundle conductor, and is externally connected with a power supply and a screen, for observing the position of seminal colliculus during operation, and positioning the membranous urethra.

In the inspection positioning prostatic capsule expansion catheter according to the present application, as the catheterization cavity has two holes in the front, drainage is more sufficient. The front bag cavity has an expansion function, and can also be used for fixing the catheter. The rear bag cavity has functions of expanding, positioning skid resistance, and protecting the seminal colliculus, and also has the function of straddling skid resistance. In addition, with positioning of an inspection probe, it is sufficient to ensure prostatic capsule expansion, so as to form a urethral gap in a bladder neck basically the same as an expansion diameter, thereby facilitating intraoperative and postoperative operations.

DETAILED DESCRIPTION

Figure 1:
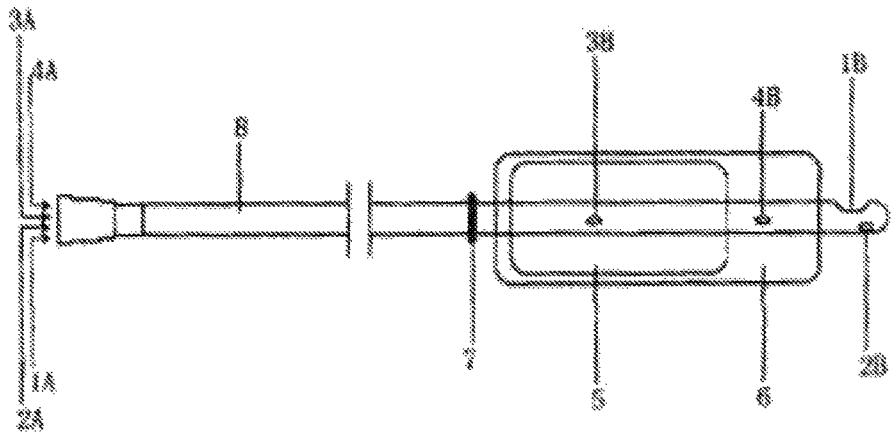
FIG. 1 is a schematic structural diagram of a prostatic splitting catheter in the prior art.
Figure 2:
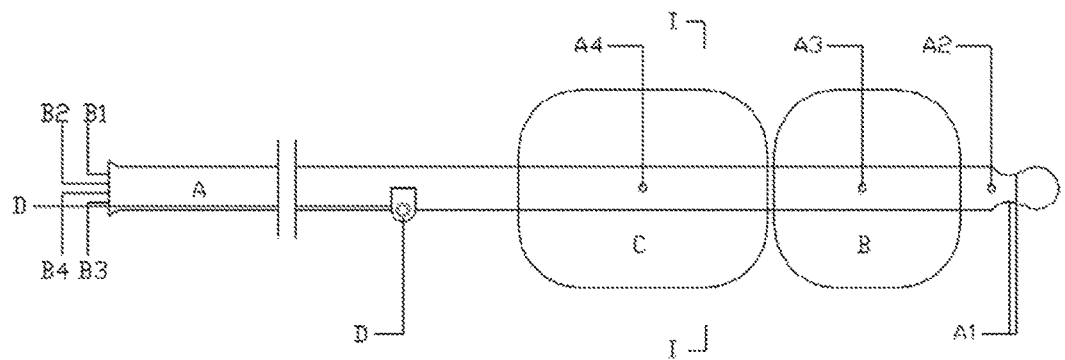
FIG. 2 is an overall schematic structural diagram of an inspection positioning prostatic capsule expansion catheter according to the present application.
Figure 3:
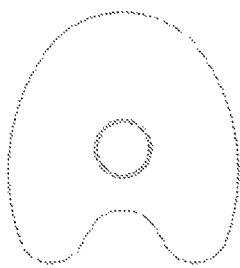
FIG. 3 is an I-I sectional view of an arched bear bag cavity after filling according to the present application.

As shown in FIG. 2 to FIG. 3, an inspection positioning prostatic capsule expansion catheter according to the present application includes a catheter main body A. The catheter main body is internally provided with a catheterization cavity, a rinse cavity, a front bag cavity, and a rear bag cavity. Front-end openings of the four cavities are A1, A2, A3 and A4, and rear-end openings are B1, B2, B3 and B4. At the rear of the front-end openings of the catheterization cavity and the rinse cavity is the front bag cavity B which is barrel-shaped after filling. At the rear of the front bag cavity is the rear bag cavity C arranged in parallel, which is barrel-shaped or arched after filling. The catheter main body at the tail of the rear bag cavity is provided with a miniature visual probe D, and the miniature visual probe D is mounted on a semi-circular protrusion at the tail of the rear bag cavity. The miniature visual probe is 1-2 cm from the tail of the rear bag cavity. The miniature visual probe D is connected with a bundle conductor, and is externally connected with a power supply and a screen.

The front-end opening A1 of the catheterization cavity is two holes, and each hole is 7 mm in length and 3-5 mm in width. The front-end opening A2 of the rinse cavity is a single hole, and the single hole is 1.5×1.5 mm square hole or a round hole with a diameter of 1.5 mm.

The catheter main body has a length of 38 cm, and an outer diameter of 0.7 cm; the front bag cavity is 3 cm in length, the rear bag cavity is 4-10 cm in length, and during filling, the front and rear bag cavities have outer diameters of 3.2-3.9 cm. As shown in FIG. 3, when the rear bag cavity is expanded to be arched, the rear bag cavity fits the seminal colliculus better; its notch surface can reduce compression on the seminal colliculus, and the rear bag cavity does not slide easily after dilatation.

The front bag cavity and the rear bag cavity both can withstand a pressure greater than or equal to 0.48 MPa. The catheter main body at the tail of the rear bag cavity is provided with a semi-circular protrusion, and the semi-circular protrusion is used as an in vitro positioning mark. The front-end openings A3 and A4 of the front bag cavity and the rear bag cavity are separately disposed on the front bag cavity B and the rear bag cavity C. Water injection catheters of their rear-end openings B3 and B4 are externally connected with two-way or three-way switches, and are then connected with pressure gauges.

In addition, a wash pipe connected to the rear-end opening B2 at the tail of the catheter main body A is 15 cm in length, a water injection catheter connected to the rear-end opening B3 of the front bag cavity is 50 cm in length, and a water injection catheter connected to the rear-end opening B4 of the rear bag cavity is 40 cm in length.

The following describes the principle of the present application with reference to the above embodiment.

The inspection positioning prostatic capsule expansion catheter according to the present application adopts a miniature visual probe, which can position expansion under direct vision and solve the problem of blind positioning, and further brings convenience to beginners, and facilitates popularity of the prostate expansion technology.

Moreover, the present application changes instability of housing one bag in the other bag in the prior art, and designs two separate high-pressure water bags, that is, a front bag cavity and a rear bag cavity. The rear bag cavity of the membranous urethra is expanded to be barrel-shaped or arched, and its notch surface can reduce compression on the seminal colliculus, and the bag cavity does not slide easily after dilatation. The front bag cavity is barrel-shaped. After the prostate gland and the bladder neck are expanded, the front bag cavity can be placed in the bladder cavity to fasten the catheter so as to prevent slippage, and can also draw hemostasis by compression. In addition, in the present application, one side hole of the front-end opening of the catheterization cavity is changed to be two side holes, which enables sufficient drainage and reduces the chances of being blocked by clots.

To sum up, the above content is merely preferred specific embodiments of the present application, and the protection scope of the present application is not limited thereto. Any variations or replacements that can be easily conceived of by persons skilled in the art without departing from the technical scope of the present application should fall within the protection scope of the present application.

What is claimed is:

1. An inspection positioning prostatic capsule expansion catheter, comprising:
   a catheter main body;
   a catheterization cavity internally provided within the catheter main body, the catheterization cavity being provided with a front-end opening (A1) adjacent a distal end of the catheter main body and a rear end opening (B1) at a proximal end of the catheter main body;
   a rinse cavity internally provided within the catheter main body, the rinse cavity being provided with a front-end opening (A2) and a rear end opening (B2) at the proximal end of the catheter main body;
   a front bag cavity internally provided within the catheter main body, the front bag cavity being provided with a front-end opening (A3) disposed in the front bag cavity and a rear end opening (B3) at the proximal end of the catheter main body;
   a rear bag cavity internally provided within the catheter main body, the rear bag cavity being provided with a front-end opening (A4) disposed in the rear bag cavity and a rear end opening (B4) at the proximal end of the catheter main body;
   wherein the front bag cavity is positioned at a rear toward the proximal end of the catheter main body of the front-end openings of the catheterization cavity and the rinse cavity, which are fixed in place on the catheter main body,
   when filled, the front and rear bag cavities have outer diameters of 3.2-3.9 cm;
   wherein the rear bag cavity is arranged at a rear of the front bag cavity such that the rear bag cavity is positioned to expand the urethra around the seminal colliculus when the front bag is placed in the bladder cavity, wherein the rear bag is arched after filling so as to provide a notch to reduce compression on the seminal colliculus after filling;
   the catheter main body at a rear of the rear bag cavity is provided with a miniature visual probe, and the miniature visual probe is mounted on a semi-circular protrusion at the tail of the rear bag cavity,
   wherein the rear bag cavity is arranged in parallel to the front bag cavity such that the rear-end opening (B3) of the front bag cavity and the rear-end opening (B4) of the rear bag cavity are externally connected with two-way or three-way switches to allow for water injection to expand the front bag cavity after the rear bag cavity has expanded.

2. The inspection positioning prostatic capsule expansion catheter according to claim 1, wherein the front-end opening of the catheterization cavity is two holes, and the front-end opening of the rinse cavity is a single hole.

3. The inspection positioning prostatic capsule expansion catheter according to claim 2, wherein the miniature visual probe is 1-2 cm from the tail of the rear bag cavity.

4. The inspection positioning prostatic capsule expansion catheter according to claim 1, wherein the catheter main body has a length of 38 cm, and an outer diameter of 0.7 cm; the front bag cavity is barrel-shaped after filling, and has a length of 3 cm; the rear bag cavity has a length of 4-10 cm.

5. The inspection positioning prostatic capsule expansion catheter according to claim 4, wherein the front bag cavity and the rear bag cavity withstand a pressure greater than or equal to 0.48 MPa.

6. The inspection positioning prostatic capsule expansion catheter according to claim 2, wherein the two holes of the front-end opening of the catheterization cavity are 7 mm in length and 3-5 mm in width, and the single hole of the front-end opening of the rinse cavity is a 1.5×1.5 mm square hole or a round hole with a diameter of 1.5 mm.

7. The inspection positioning prostatic capsule expansion catheter according to claim 4, wherein a wash pipe connected to a rear-end opening at a tail of the catheter main body is 15 cm in length, a water injection catheter connected to a rear-end opening of the front bag cavity is 50 cm in length, and a water injection catheter connected to a rear-end opening of the rear bag cavity is 40 cm in length.

8. The inspection positioning prostatic capsule expansion catheter according to claim 6, wherein a wash pipe connected to a rear-end opening at a tail of the catheter main body is 15 cm in length, a water injection catheter connected to a rear-end opening of the front bag cavity is 50 cm in length, and a water injection catheter connected to a rear-end opening of the rear bag cavity is 40 cm in length.

9. The inspection positioning prostatic capsule expansion catheter according to claim 4, wherein water injection catheters of rear-end openings of the front bag cavity and the rear bag cavity are externally connected with pressure gauges.

10. The inspection positioning prostatic capsule expansion catheter according to claim 6, wherein water injection catheters of rear-end openings of the front bag cavity and the rear bag cavity are externally connected with pressure gauges.

\* \* \* \* \*